United States Patent [19]

Lao

[11] 4,072,046
[45] Feb. 7, 1978

[54] ACOUSTIC PYCNOMETER

[75] Inventor: Binneg Yanbing Lao, Midland, Mich.

[73] Assignee: The Dow Chemical Company, Midland, Mich.

[21] Appl. No.: 720,480

[22] Filed: Sept. 3, 1976

[51] Int. Cl.² ............................................ G01M 17/00
[52] U.S. Cl. .......................................... 73/574; 73/149; 73/571
[58] Field of Search ................ 73/67, 67.1, 69, 149, 73/299 B, 290 V, 67.2

[56] References Cited

U.S. PATENT DOCUMENTS 2,584,128  2/1952  Hildyard .......................... 73/290 B
3,075,382  1/1963  Mathias ............................. 73/149

FOREIGN PATENT DOCUMENTS 663,946  1/1952  United Kingdom ............... 73/290 B Primary Examiner—James J. Gill
Attorney, Agent, or Firm—Earl D. Ayers

[57] ABSTRACT

An improved pycnometer in which the sample whose volume to be measured is put in a closed chamber to which an electro-mechanical transducer is coupled. The transducer is excited at a constant frequency. The change in impedance of the transducer is then read as a function of the volume of the sample.

4 Claims, 2 Drawing Figures

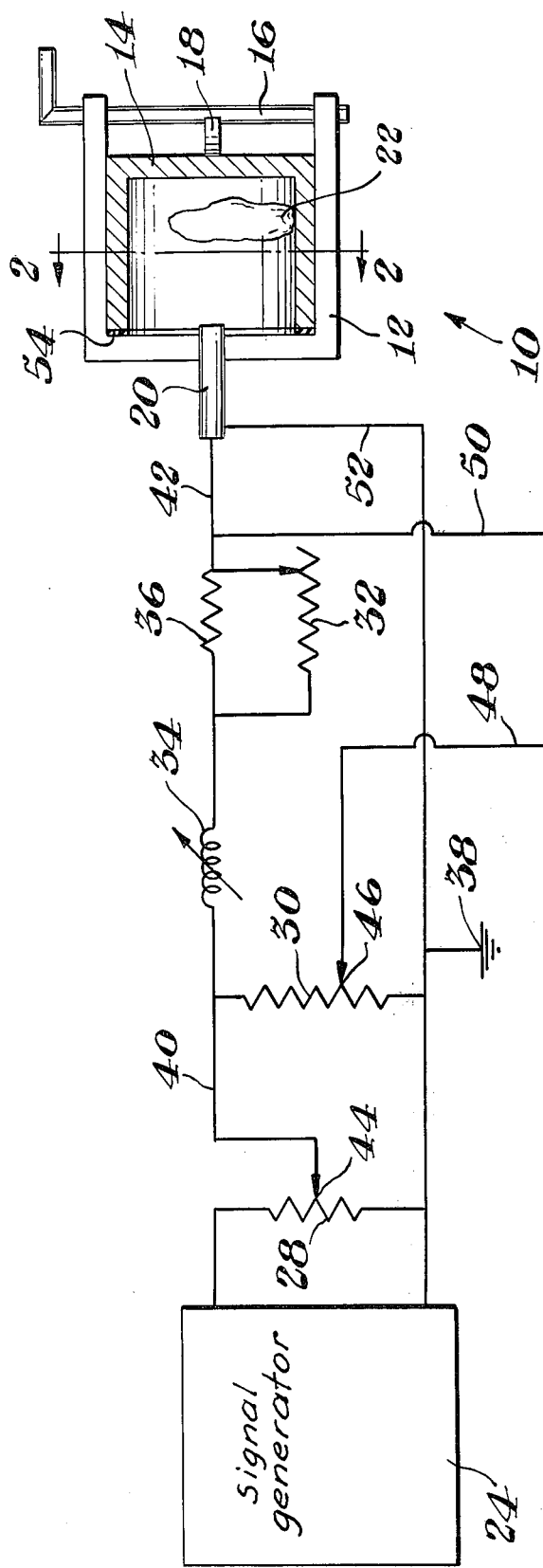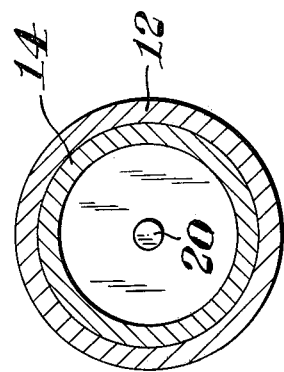
Fig. 1
Fig. 2

ACOUSTIC PYCNOMETER

BACKGROUND OF THE INVENTION

This invention relates to apparatus for measuring the volume of a solid sample, and particularly to acoustic pycnometers.

Standard means for measuring volumes (of up to a few cubic feet) include the air pycnometer or liquid immersion volume measuring apparatus.

Such means are either relatively slow to operate, wet the sample, have moving parts, subject the sample to pressure, or cannot be operated remotely to handle sterile or toxic objects.

OBJECTS OF THE INVENTION

A principal object of this invention is to provide an improved, easier to use pycnometer.

Another object of this invention is to provide an improved, direct reading acoustic pycnometer.

A further object of this invention is to provide an improved acoustic pycnometer which has no moving parts during operation of the device.

An additional object of this invention is to provide an improved, faster acting pycnometer.

STATEMENT OF INVENTION

In accordance with this invention, there is provided an improved pycnometer having an enclosable sample chamber into which an electro-mechanical transducer is coupled, means for exciting the transducer at a constant frequency, and means for measuring the electrical impedance of the transducer as a function of the volume of a sample in the chamber.

BRIEF DESCRIPTION OF THE DRAWING

The invention, as well as additional objects and advantages thereof, will best be understood when the following detailed decription is read in connection with the accompanying drawing, in which:

FIG. 1 is a diagrammatical view, partly in section, of pycnometer apparatus in accordance with this invention, and FIG. 2 is a sectional view along the line 2—2 of FIG. 1.

DETAILED DESCRIPTION OF THE DRAWING

Referring to the drawing, there is shown pycnometer apparatus, indicated generally by the numeral 10 composed of a cup shaped frame 12 having a flat bottom through which an electro-mechanical transducer 20 is coupled. Another cup 14 has outer walls which fit closely but slidably within the cup 12 with its open end abutting against the deformable ring seal 54 at the closed end of the cup 12.

The cup 14 is held against the bottom of the cup 12 by wedging means 18 extending from the pin 16 which is secured to the cup 12 near the open end of the cup.

The electro-mechanical transducer 20 is excited or energized by the electronic signal generator 24 through the lead 52 which is grounded, as at 38 and through lead 42.

Lead 42 is coupled to resistance 36 which in turn is coupled through variable inductance 34 to the lead 40 which is coupled to the movable contact of the voltage divider 28 which is coupled across the output of the signal generator 24. One output lead from the generator 24 is grounded (at 38) through lead 52 which is also coupled to the transducer 20.

A second potentiometer 30 is coupled between ground and the lead 40 between the inductance 34 and the contact 44 with its moving contact 46 being coupled to one input of a millivoltmeter 26 through lead 48.

The other lead 50 to the input of the millivoltmeter 26 is coupled to the lead 42 between the resistance 36 and the transducer 20.

A variable resistor 32 is coupled across the resistor 36.

OPERATION

In operation, the inductance 34 and resistance elements 36, 32 act as one arm of a bridge circuit, the transducer 20 acts as an opposing arm while resistance 30 divided in two at 46 acts as the other two arms of the bridge circuit 46 is normally set at midpoint of 30.

The millivoltmeter 26 is connected "across the bridge."

With the sample receiving chamber empty and closed the signal generator energizing the entire bridge, the inductance 34 and variable resistance 32 are adjusted to give a null reading on the millivoltmeter.

The chamber is then closed with a sample 22 inside, and the reading of the millivoltmeter noted. The reading of the meter 26 is a function of sample volume and the meter scale may, if desired, directly read in volume units.

The cup like parts 12, 14 of the chamber may fit rather loosely provided the rim of the part 14 fits in sealing relationship with the gasket 54 at the bottom of the part 12. The walls of the part 12 need only to provide means for use in urging a sealing relationship between the part 14 and bottom of the part 12.

The signal generator 24 preferably provides a signal whose wave length is greater than ¼ the length of the longest dimension of the sample chamber.

In practice, the wavelength is usually about ten times the length of the largest dimension of the sample chamber, or greater.

The transducer 20, for small sample chambers, may be a dynamic microphone. Alternatively, a device such as a small dynamic loudspeaker may be used.

Sample volume measurement has been found to be independent of sample positioning and the physical shape of the sample.

The device is well adapted for use in remote measuring the volume of toxic or radioactive materials as well as measuring the volume of metal or plastic objects of solid or foamed structure.

One signal generator used is a Hewlett Packard 200 CD unit, but other similar devices may be used.

What is claimed is:

1. Pycnometer apparatus comprising an enclosable chamber for receiving a sample whose volume is to be measured, an electro-acoustical transducer coupled to the interior of said chamber, electronic signal generator means for electrically energizing said transducer at a predetermined frequency having a wave length at least four times the longest dimension of said chamber, electrical bridge circuit means coupled between said means for electrically energizing and said electro-mechanical transducer, said bridge circuit including means for nulling the signal across said bridge circuit when said chamber is empty, and means for reading the signal across said bridge when a sample is disposed in said chamber, the magnitude of said signal being a function of the volume of the sample.

2. Apparatus in accordance with claim 1, wherein said electro-mechanical transducer is a dynamic microphone or dynamic speaker.

3. Apparatus in accordance with claim 1, wherein said means for nulling said signal includes a variable inductance and variable resistance.

4. Apparatus in accordance with claim 1, wherein said chamber includes opening and closing means.

* * * * *